(12) United States Patent
Schadewaldt et al.

(10) Patent No.: US 11,285,338 B2
(45) Date of Patent: Mar. 29, 2022

(54) RADIOTHERAPY PLANNING WITH IMPROVE ACCURACY

(71) Applicant: KONINKLIJKE PHILIPS N. V., Eindhoven (NL)

(72) Inventors: Nicole Schadewaldt, Norderstedt (DE); Steffen Renisch, Hamburg (DE); Sven Prevrhal, Hamburg (DE); Heinrich Schulz, Hamburg (DE); Thomas Blaffert, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 846 days.

(21) Appl. No.: 15/565,697

(22) PCT Filed: Apr. 12, 2016

(86) PCT No.: PCT/EP2016/057953
§ 371 (c)(1),
(2) Date: Oct. 11, 2017

(87) PCT Pub. No.: WO2016/166071
PCT Pub. Date: Oct. 20, 2016

(65) Prior Publication Data
US 2018/0078787 A1  Mar. 22, 2018

(30) Foreign Application Priority Data

Apr. 14, 2015  (EP) ..................... 15163484

(51) Int. Cl.
*A61N 5/10* (2006.01)
*A61B 5/055* (2006.01)

(52) U.S. Cl.
CPC ............ *A61N 5/1039* (2013.01); *A61B 5/055* (2013.01); *A61N 2005/1074* (2013.01)

(58) Field of Classification Search
CPC ............ A61B 5/055; A61N 2005/1074; A61N 5/1039
See application file for complete search history.

(56) References Cited

U.S. PATENT DOCUMENTS 5,204,625 A * 4/1993 Cline ..................... G01R 33/56
324/306
8,421,038 B2  4/2013 Remeijer et al.
(Continued)

OTHER PUBLICATIONS

Ramsey et al. (Magnetic resonance imaging based digitally reconstructed radiographs, virtual simulation, and three-dimensional treatment planning for brain neoplasms, Med. Phys. 25 .10., 1928-1934, Oct. 1998) (Year: 1998).*

(Continued)

*Primary Examiner* — Pascal M Bui Pho
*Assistant Examiner* — Alexei Bykhovski
(74) *Attorney, Agent, or Firm* — Sherry Austin (57) ABSTRACT

The present disclosure relates to a method for controlling a magnetic resonance imaging guided radiation therapy apparatus comprising a magnetic resonance imaging system. The method comprises: acquiring magnetic resonance data using the magnetic resonance imaging system and the pulse sequence from an imaging volume; segmenting the magnetic resonance data into a plurality of segments indicating respective tissues in the imaging volume; creating a bulk electron density map of the imaging volume from the plurality of segments; displaying the bulk electron density map and radiation dose distributions for the plurality of segments on a graphical user interface, wherein the radiation dose distributions are determined using the bulk electron density map; receiving a modification signal for modifying at least a first segment of the segments; recreating the bulk electron density map using the modified first segment, and recalculating the radiation dose distribution using the bulk (Continued)

electron density map; redisplaying the bulk electron density map and the radiation dose distributions on the graphical user interface.

20 Claims, 3 Drawing Sheets

(56) References Cited

U.S. PATENT DOCUMENTS

| | | | |
|---|---|---|---|
| 8,787,648 B2 | 7/2014 | Schulz et al. | |
| 2007/0263769 A1 | 11/2007 | Roell | |
| 2008/0132787 A1 | 6/2008 | Putaala | |
| 2011/0007959 A1* | 1/2011 | Schulz | A61B 5/055 382/131 |
| 2011/0178389 A1* | 7/2011 | Kumar | A61B 5/055 600/411 |
| 2014/0296696 A1 | 10/2014 | Remmele et al. | |
| 2015/0126799 A1 | 5/2015 | Vahala | |
| 2016/0225146 A1* | 8/2016 | Frank | A61B 5/055 |
| 2016/0279445 A1 | 9/2016 | Ju | |
| 2016/0320466 A1* | 11/2016 | Berker | G01R 33/5608 |

OTHER PUBLICATIONS

Dowling et al "Automatic MRI Atlas-Based External Beam Radiation Therapy Treatment Planning for Prostate Cancer" Prostate Cancer Imaging, Sep. 24, 2010 p. 25-33.

Michael Helle, Nicole Schadewaldt, et al. 'Evaluation of Dixon based Soft Tissue and Bone Classification in the pelvis for MR only based Radiation Therapy Planning', abstract accepted at ISMRM 2014.

Adam Johansson, Mikael Karlsson and Tufve Nyholm, CT substitute derived from MRI sequences with ultrashort echo time. In Medical Physics 38 (5) May 2011.

Na, Yong Hum, et al. "Toward a web-based real-time radiation treatment planning system in a cloud computing environment." Physics in medicine and biology 58.18 (2013): 6525.

Kirisits et al. "Dose and Volume Parameters for MRI-based Treatment Planning in Intracavitary . . ." Int. J. Radiation Oncology Biol. Phys. vol. 62, No. 3, pp. 901-911 (2005).

Jonsson et al "Treatment Planning Using MRI Data: An Analysis of the Dose Calculation Accuracy for Different Treatment Regions" Radiation Oncology 2010, 5:62.

* cited by examiner

RADIOTHERAPY PLANNING WITH IMPROVE ACCURACY

CROSS REFERENCE TO RELATED APPLICATIONS

This application is a U.S. national phase application of International Application No. PCT/EP2016/057953, filed on Apr. 12, 2016, which claims the benefit of EP Application Serial No. 15163484.7 filed on Apr. 14, 2015 and is incorporated herein by reference.

TECHNICAL FIELD OF THE INVENTION

The invention relates to energy treating devices, in particular to the use of a therapy system for radiotherapy planning with improved accuracy.

BACKGROUND OF THE INVENTION

Creating estimated electron density maps from magnetic resonance (MR) images is a problem that occurs, e.g., with integrated positron emission tomography (PET)/MR systems, where an attenuation map needs to be estimated for the attenuation correction of the PET images, or with radiation therapy planning based on MR, where electron density maps are required for the treatment simulation. However, due to the physics of the image acquisition, MR intensities do not uniquely correspond to electron density. Hence those maps when derived from the MR image by, e.g., a lookup operation, as is commonly done when estimating these maps from computed tomography (CT) images, may not be accurate.

The U.S. Pat. No. 8,787,648. mentions that an atlas is populated with CT and MRI reference images, which are registered manually on the basis of anatomical landmarks. A new patient MRI image is registered to one of the MRI reference images. This registration also registers to the associated CT images and in this manner CT intensity information is provided to the new patient MRI images.

SUMMARY OF THE INVENTION

Various embodiments provide for a magnetic resonance imaging guided radiation therapy apparatus, an improved method, and a computer program product as described by the subject matter of the independent claims. Advantageous embodiments are described in the dependent claims.

In one aspect, the invention relates to a magnetic resonance imaging guided radiation therapy apparatus (the apparatus), comprising:
 a magnetic resonance imaging system;
 a processor for controlling the apparatus; and
 a memory containing machine executable instructions and a pulse sequence,
wherein execution of the instructions causes the processor to:
a) acquire magnetic resonance data using the magnetic resonance imaging system and the pulse sequence from an imaging volume;
b) segment the magnetic resonance data into a plurality of segments indicating respective tissues in the imaging volume;
c) create a bulk electron density map of the imaging volume from the plurality of segments;
d) display the bulk electron density map and radiation dose distributions for the imaging volume on a graphical user interface, wherein the radiation dose distributions are determined using the bulk electron density map;
e) receive a modification signal for modifying at least a first segment of the segments;
f) recreate the bulk electron density map using the modification signal, and recalculate the radiation dose distribution using the recreated bulk electron density map;
g) redisplay the recreated bulk electron density map and the recalculated radiation dose distributions on the graphical user interface;
h) use the displayed (recreated) electron density map and the (recalculated) radiation dose distributions for controlling the irradiation of at least part of the imaging volume.

Step g) may further comprise prompting a user of the apparatus for an acknowledgement of the displayed (recreated) electron density map and the (recalculated) radiation dose distributions, wherein step h) is performed upon receiving the acknowledgement. If for example, the acknowledgement is not received after a predefined time interval, steps e)-g) may be repeated.

In another example, step h) may automatically be performed if the time elapsed since the display of step g) is performed is higher than a predefined time period.

Step d) may further comprise prompting the user for a modification of at least a first segment of the segments.

The bulk electron density map (also referred to as a synthetic CT image or MR Calculated ATtenuation (MR-CAT) image) is reconstructed from a plurality of reconstructed MR images from the acquired MR data and/or the acquired MR data on the basis of electron density and tissue characterisation/classification. One possible implementation is the reconstruction of a water, a fat and an inphase image from the acquired MR data with a DIXON reconstruction algorithm. The water and fat images are used to determine water and fat voxels in the image. Both images are also used to segment bony structures with a model based segmentation technique. The inphase image is then used to differentiate between cortical and cancellous bone within the segmented area via a threshold. An additional threshold will determine the body outline. This would lead to an image with 5 tissue classes (air, fat, water, cancellous bone and cortical bone) using several reconstructed images from the raw MR data. Other tissue classes are possible (e.g. treating each bone separately due to density differences) and other segmentation methods using other images are possible (e.g. segmentation of important structures on a different MR image, e.g. a T2 images).

The above features may enable to provide better control of the radiation dose distribution and to provide insight in the accuracy of the synthetic CT image as a basis for computing the radiation dose distribution. The present method may provide alternatives to calculate the radiation dose distribution if e.g. the shape of the segments or tissues is not accurate.

If an obvious error or inaccuracy (e.g. related to the shape or the bulk electron density of a segment) is present in the bulk electron density map, this may or may not alter the radiation dose distribution compared to a radiation dose distribution of a correct MR-CAT image. E.g. a large misclassification of tissue as cortical bone due to a segmentation error will significantly alter radiation dose in other parts of the image, if the radiation beam passes through that area, but will not change the radiation dose in the other parts of the image, if this region is not being irradiated.

Another advantage may be that the present method may save resources and processing time by allowing radiation dose planning on the MR image and thus avoiding a CT image acquisition and reconstruction. This is in contrast to a conventional method where in addition to a MR procedure a CT based procedure is required for an accurate radiotherapy planning, which is the current standard e.g. for prostate radiation therapy planning Other advantages of the present method may be that the method may:

adapt non-perfect MR-CAT images such that they become suitable for therapy planning;

assess the influence of certain changes to MR-CAT images; gain experience with the kind of changes, that influence radiation dose distributions; and provide a reliable a system for radiotherapy planning without using a CT image.

According to one embodiment, execution of the instructions further causes the processor to repeat steps e)-g) until receiving a confirmation of the bulk electron density map. This may further increase the reliability and accuracy of the radiotherapy planning For example, in a given iteration the display of the bulk electron density map may further indicate the difference between the radiation dose distribution of the present iteration and the radiation dose distribution of a (immediate) previous iteration or of the initially displayed electron density map. The confirmation is received based on the displayed difference. For example, if the difference is smaller than a predetermined maximum allowed shift value the confirmation may be received.

According to one embodiment, the first segment comprises a first set of voxels having respective first values indicative of a first tissue of the imaging volume, wherein receiving the modification comprises: receiving a selection of one or more voxels of the first set of voxels; wherein the selection is indicative of a second value for each of the selected voxels, the second value indicating a second tissue of the imaging volume; replacing the first values by the second values for the selected voxels. This may further improve the control of the radiation dose distribution and to provide insight in the accuracy of the synthetic CT image as a basis for computing the radiation dose distribution. A voxel is an individual element of the MR image.

Further, the selection of the one or more voxels may comprise entering or inputting the second value e.g. via an input field of the graphical user interface. Then the selected voxels would not be assigned to one of the other segments respective tissue classes, but to a new instance defined by the second value entered.

According to one embodiment, the first segment comprises a first set of voxels having respective first values indicative of a first tissue of the imaging volume, wherein receiving the modification comprises: receiving a selection of one or more voxels of the first set of voxels; wherein the selection is indicative of a maximum value; in case a first value of a voxel of the selected voxels is higher than the maximum value replacing that first value by the maximum value, wherein the maximum value is indicative of a second tissue of the imaging volume.

According to one embodiment, the first segment comprises a first set of voxels having respective first values indicative of a first tissue of the imaging volume, wherein receiving the modification comprises: receiving a selection of one or more voxels of the first set of voxels; wherein the selection is indicative of a minimum value; in case a first value of a voxel of the selected voxels is smaller than the maximum value replacing that first value by the minimum value, wherein the minimum value is indicative of a third tissue of the imaging volume.

According to one embodiment, the first segment comprises a first set of voxels having respective first values indicative of a first tissue of the imaging volume, wherein receiving the modification comprises: receiving a selection of one or more voxels of the first set of voxels; and removing selected voxels of the first segment and assigning a third value to the selected voxels.

According to one embodiment, the modification of the first segment is received by detecting (e.g. by a sensor) movement of a cursor of the graphical user interface onto at least part of the first segment for the selection of the at least part of the first segment.

The detecting may comprise determining a direction line of the movement of the cursor and starting and ending point of the movement on the bulk electron density map. The one or more voxels may be positioned along the direction line between the starting and ending points.

According to one embodiment, the graphical user interface is displayed on a display device of the apparatus, wherein the display device comprises a touch sensitive display device, the apparatus further comprising a sensor wherein the reception of the modification comprises: detecting by the sensor a touch action on the display device indicative of the modification.

According to one embodiment, the apparatus further comprises pen entry means comprising an entry pen wherein the touch action is performed by orienting the entry pen towards the at least part (e.g. the one or more voxels) of the first segment without contacting the display device.

For example, using the entry pen or the cursor a user may select either a pen graphical user interface (GUI) element or an eraser GUI element. Based upon whether the pen GUI element or the eraser GUI element is selected, the cursor in the display device changes to pen or eraser, respectively. Receiving a selection of the one or more voxels via the pen GUI element may indicate that the values of the selected one or more voxels may be replaced by other values e.g. in order to be assigned to a selected tissue. Receiving a selection of the one or more voxels via the eraser GUI element may indicate that the selected one or more voxels may be deleted from the first segment e.g. being assigned to a default tissue, or to a background tissue or without being assigned to another tissue. A background tissue may be chosen based on the reconstructed MR images, e.g. the water and fat images enables to label each voxel as water and fat, thus the background value could be chosen according to this labelling, if any other tissue (cortical or cancellous bone, air) is removed with the eraser tool.

According to one embodiment, the touch action comprises pen interaction of the entry pen with the display device, or a user finger touch of the display device.

According to one embodiment, the touch action comprises a drag action having a starting point and an ending point in the first segment, wherein the modification is performed along a line between the starting and ending points.

According to one embodiment, execution the instructions further causes the processor to: display a MR image of the imaged volume before receiving the confirmation. The modification is performed using the MR image.

According to one embodiment, the repeating of steps e)-g) is performed for a second segment different from the first segment.

In another aspect, the invention relates to a computer program product comprising computer executable instructions to perform the method steps of the above method.

In another aspect, the invention relates to a method for controlling a magnetic resonance imaging guided radiation therapy apparatus comprising a magnetic resonance imaging system, the method comprising:

a) acquiring magnetic resonance data using the magnetic resonance imaging system and the pulse sequence from an imaging volume;
b) segmenting the magnetic resonance data into a plurality of segments indicating respective tissues in the imaging volume;
c) creating a bulk electron density map of the imaging volume from the plurality of segments;
d) displaying the bulk electron density map and radiation dose distributions for the plurality of segments on a graphical user interface, wherein the radiation dose distributions are determined using the bulk electron density map;
e) receiving a modification signal for modifying at least a first segment of the segments;
f) recreating the bulk electron density map using the modified first segment, and recalculating the radiation dose distribution using the bulk electron density map;
g) redisplaying the bulk electron density map and the radiation dose distributions on the graphical user interface;
h) using the displayed electron density map and the radiation dose distributions for controlling the irradiation of at least part of the imaging volume.

Magnetic resonance image data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

In the following, like numbered elements in the figures are either similar elements or perform an equivalent function. Elements which have been discussed previously will not necessarily be discussed in later figures if the function is equivalent.

Various structures, systems and devices are schematically depicted in the figures for purposes of explanation only and so as to not obscure the present invention with details that are well known to those skilled in the art. Nevertheless, the attached figures are included to describe and explain illustrative examples of the disclosed subject matter.

Figure 1:
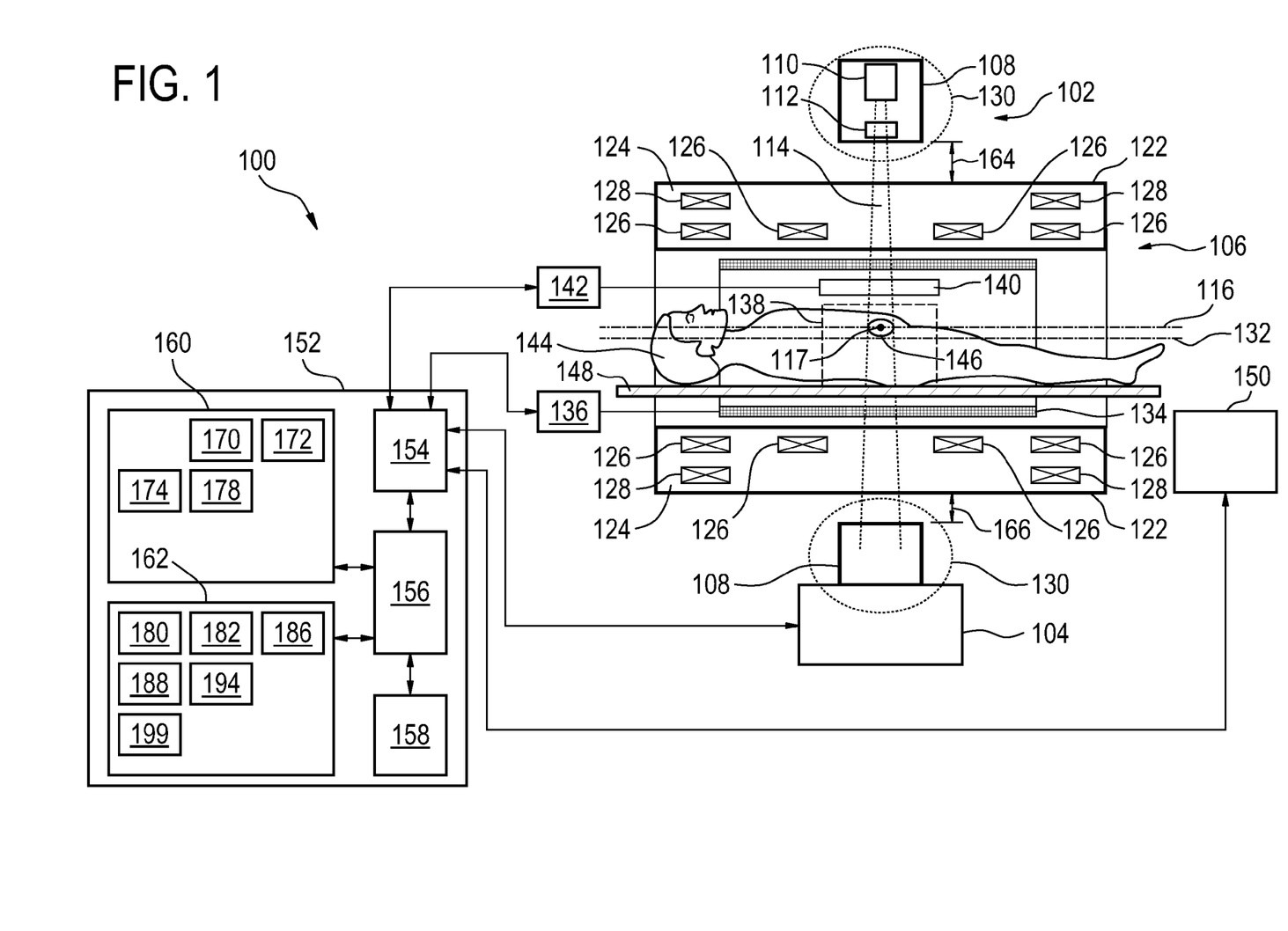
FIG. 1 shows a cross-sectional and functional view of a therapy system.

FIG. 1 shows a cross-sectional and functional view of a therapy system 100. The therapy system 100 is shown as comprising a radiotherapy apparatus 102 and a magnetic resonance imaging module 106. The radiotherapy apparatus 102 comprises a ring mechanism 108. The ring mechanism 108 supports a radiotherapy source 110. The radiotherapy source 110 is representative and may be a LINAC x-ray source, an x-ray 2 and a radioisotope gamma radiation source. Adjacent to the radiotherapy source 110 is a multi-leaf beam collimator 112 for collimating a radiation beam 114 that is generated by the radiotherapy source 110. The ring mechanism 108 is also adapted for moving e.g. rotating the radiotherapy source 110 and the beam collimator 112 about a rotational point 117 of the radiotherapy apparatus 102. A rotational axis 116 passes through the rotational point 117.

The magnetic resonance imaging module 106 is shown as comprising a main magnet 122. The ring mechanism 108 is ring-shaped and surrounds the main magnet 122. The main magnet 122 shown in FIG. 1 is a cylindrical type superconducting magnet. However, other magnets are also applicable for embodiments of the invention. The main magnet 122 has a supercooled cryostat 124. Inside the cryostat 124 there is a collection of superconducting coils 126. There are also compensation coils 128 whose current opposes the direction of current in the superconducting coils 126. This creates a low magnetic field zone 130 that circles or encompasses the main magnet 122. The cylindrical main magnet 122 is shown as having an axis 132 of symmetry.

Within the bore of the magnet there is a magnetic field gradient coil 134 which is used for acquisition of image magnetic resonance data to spatially encode objects within an imaging volume 138 of the main magnet 122. The magnetic field gradient coil 134 is connected to a magnetic field gradient coil power supply 136. The magnetic field gradient coil 134 is intended to be representative. Typically magnetic field gradient coils contain three separate sets of coils for spatially encoding in three orthogonal spatial directions. The imaging volume 138 is located in the center of the main magnet 122.

Adjacent to the imaging volume 138 is a radio frequency (RF) coil 140 for manipulating the orientations of magnetic spins within the imaging volume 138 and for receiving radio transmissions from spins also within the imaging volume 138. The radio frequency coil 140 is connected to a radio frequency transceiver 142. The radio frequency coil 140 and radio frequency transceiver 142 may be replaced by separate transmit and receive coils and a separate transmitter and receiver. It is understood that the radio frequency coil 140 and the radio frequency transceiver 142 are simply representative.

Within the center of the main magnet 122 is also located a subject 144. The subject 144 has a target volume (or target zone) 146 and is shown as reposing on a patient carrier 148. The RF coil 140 may transmit RF pulses into the target volume 146. The patient carrier 148 has a mechanical positioning system 150. The mechanical positioning system 150 is adapted for positioning the patient carrier 148 within the main magnet 122. Depending upon the space available inside of the main magnet 122, the mechanical positioning system 150 may move the patient carrier 148 in different directions including a direction perpendicular to the magnet axis 132. If there is more space available inside the main magnet 122 the mechanical positioning system 150 may have more degrees of freedom. For instance the mechanical positioning system 150 may position the patient carrier 148 with six degrees of freedom.

The radio frequency transceiver 142, the magnetic field gradient coil power supply 136, the mechanical actuator 104, and the mechanical positioning system 150 are all shown as being connected to a hardware interface 154 of a computer system 152. The computer system 152 uses a processor 156 to control the therapy system 100.

The computer system 152 shown in FIG. 1 is representative. Multiple processors and computer systems may be used to represent the functionality illustrated by this single computer system 152. The computer system 152 comprises the hardware interface 154 which allows the processor 156 to send and receive messages to components of the therapy system 100. The processor 156 is also connected to a display device 158, computer storage 160, and computer memory 162. The display device 158 may comprise a touch screen sensitive display device. The display device may be provided with a detachable stylus pen to allow a user to more efficiently manipulate the display device 158.

The radiotherapy apparatus 102 is not shown as being connected to the hardware interface 154. The radiotherapy apparatus 102 may be, for example, connected to the hardware interface 154 and communicates with the computer system 152 via the mechanical actuator 104.

For the example shown in FIG. 1, the rotational axis 116 of the radiotherapy apparatus is not coaxial with the magnet axis 132. The rotational point 117 is shown as being off center from the magnet axis 132. It can be seen that the target zone 146 is off-center and away from the magnet axis 132. The radiotherapy apparatus 102 has been moved by mechanical actuator 104 such that the rotational point 117 of the radiotherapy apparatus is within the target zone 146. It can be seen that the ring mechanism 108 has been moved relative to the magnet 122.

The radiation beam 114 passes through the rotational point 117. Placing the rotational point 117 at the center of the target zone 146 allows the target zone to be treated continuously when the radiation beam 114 is created by the radiotherapy source 110 and is rotated by the ring mechanism 108.

Computer storage 160 is shown as containing image magnetic resonance data 170 that have been acquired by the magnetic resonance imaging module 106. The computer storage 160 is shown as further containing diagnostic images (i.e. image representation) 172 that have been reconstructed from the image magnetic resonance data. The computer storage 160 is shown as further containing coordinates 174 of the target volume 146. The computer storage 160 is shown as further containing radiotherapy control signals 178.

The computer memory 162 contains machine executable instructions 180, 182, 186, 188, 194 for operation by the processor 156. The computer memory 162 is shown as containing a therapy system control module 180. The therapy system control module 180 contains machine executable instructions which allow the processor 156 to control the overall functioning of the therapy system 100. The computer memory 162 is shown as further containing a radiotherapy apparatus control module 182. The radiotherapy apparatus control module 182 contains machine executable instructions which allow the processor 156 to control the functioning of the radiotherapy apparatus 102.

The computer memory 162 is shown as further containing a magnetic resonance imaging control module 186. The magnetic resonance imaging control module 186 contains machine executable code which allows the processor 156 to control the functioning and operation of the magnetic resonance imaging module 106. The computer memory 162 is shown as further containing an image reconstruction module 188. The image reconstruction module 188 contains machine executable code which is used by the processor 156 to transform the image magnetic resonance data 170 into images 172.

The computer memory 162 is shown as further containing radiotherapy control signal generation module 194. The radiotherapy control signal generation module 194 contains computer executable code which the processor 156 uses to generate the radiotherapy control signals 178. The radiotherapy control signals 178 may be generated in conjunction with the coordinates 174 of the target volume 146.

The computer memory 162 is shown as further comprising an algorithm 199. The algorithm 199 contains computer executable code which the processor 156 uses to detect discrepancies or anomalies in segmented MR images (and classified into tissues) by using reference images or reference data. For example, the algorithm 199 may be configured to compare the size of a bone segment or tissue in the segmented MR image with a reference diameter (of the reference data) that the bone tissue should not exceed. By identifying a discrepancy (e.g. the size exceeds the diameter) the algorithm 199 may request a modification of the segmented MR image.

In another example, since most structures of clinical interest have a known characteristic shape and anatomical location relative to other structures, the analysis of the segmented MR image using those characteristics may trigger the algorithm to request a modification of the segmented MR image. The analysis may be performed by for example aligning an MR image taken now with one taken on a previous occasion or aligning images of two objects that are expected a priori to be the same.

The computer memory 162 further contains computer-executable code which enables the processor 156 to execute at least part of the below described method.

The system of the present disclosure is not limited to a combined radiotherapy apparatus and a MRI module as shown with reference to FIG. 1. For example, the present disclosure may be applied using a MRI system only e.g. to obtain an electron density map as described herein.

Figure 2:
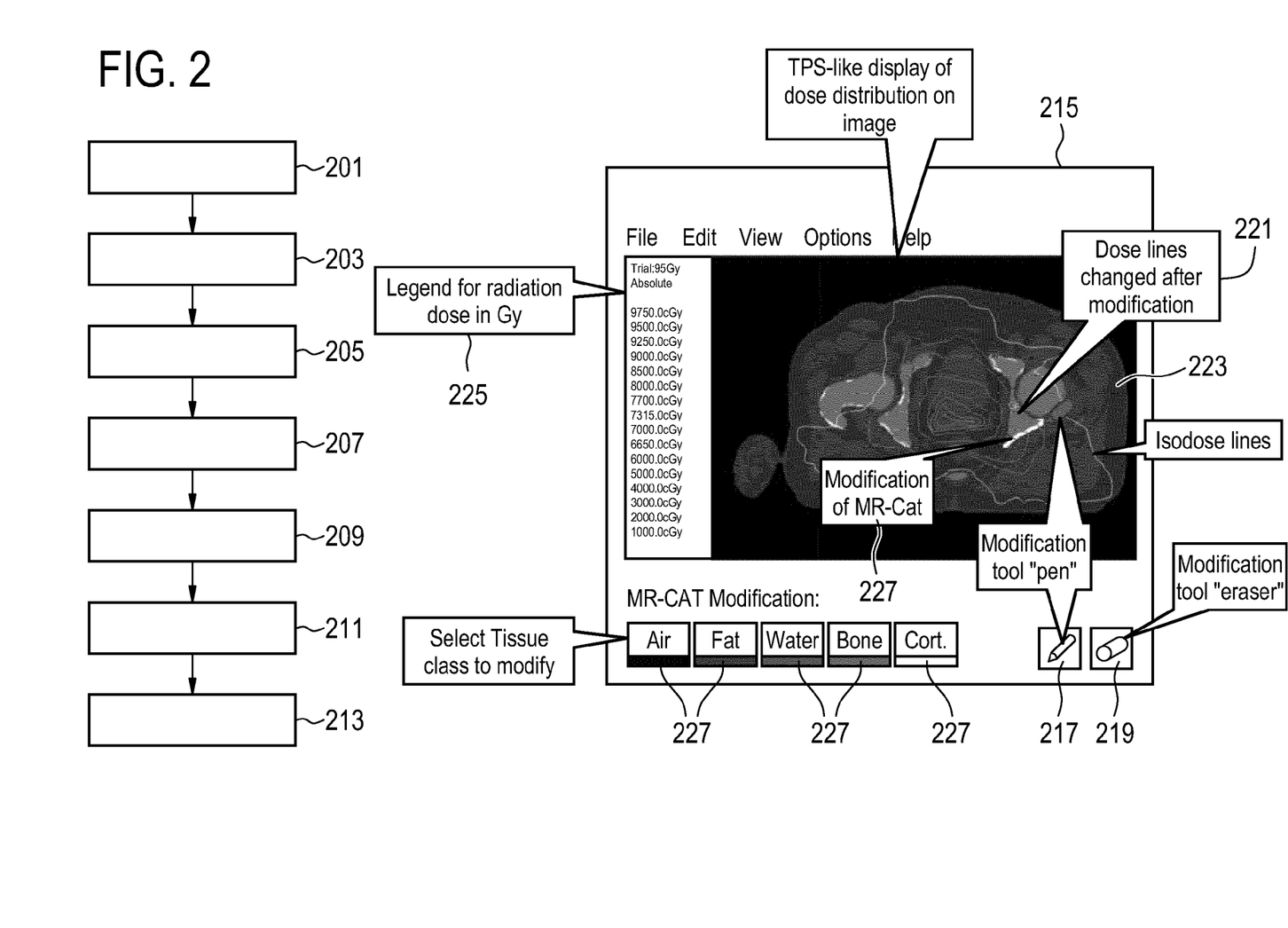
FIG. 2 is a flowchart of a method for a therapy procedure.

FIG. 2 is a flowchart of a method for providing a radiotherapy plan. The radiotherapy plan may indicate for example direction, intensity and/or shape of radiation beam 114.

In step 201, magnetic resonance data may be acquired using the magnetic resonance imaging module or system 106 and the pulse sequence from an imaging volume e.g. 138. The pulse sequence may comprise for example a spin echo MRI pulse sequence or a T1-weighted gradient echo sequence.

In step 203, the acquired magnetic resonance data may be segmented into a plurality of segments indicating respective tissues in the imaging volume. A tissue may for example comprise a fat, water, bone or air tissue etc. For example, the segmenting may be performed by generating segments corresponding to bone, air and soft tissue (e.g., a water segment and a fat segment) by segmenting respective voxels. For example, the bone segment may comprise a first set of voxels that indicate the bone tissue.

In one example, the segmenting may be performed by reconstructing an MR image using the acquired MR data, and segmenting the reconstructed MR image. The segmenting may comprise dividing up the reconstructed MR image into a patchwork of regions or segments each of which is homogenous e.g. in term of intensity and/or texture. The segmenting comprises the tissue classification. For example, the segmenting comprises assigning to each individual element of the reconstructed MR image a tissue class indicating the tissue into which belongs the individual element. The individual element may comprise a voxel. The tissue class may be assigned to the individual element by for example assigning a value e.g. number, specific to that tissue class. For example, each individual element of the MR image may be classified according to its probability of being a member or part of a particular tissue class.

In another example, the segmenting may be performed using the acquired MR data e.g. for determining water and fat segments as done by the Dixon-reconstruction algorithm.

In step 205, a bulk electron density map of the imaging volume may be created from the plurality of segments. For example, the electron density map may be created by assigning a bulk electron density to various tissues or segments of the imaging volume as found in the segmenting step. For example, a bulk electron density of 0 g/cm$^3$ may be assigned to the air segment or tissue, 1.5 g/cm$^3$ for bone tissues etc. The bulk electron density values (also referred to as electron density values) may be predefined values.

In step 207, radiation dose distributions may be calculated using the bulk electron density map. The radiation dose distributions may be displayed (e.g. in form of contours or dose lines 221) on top of the electron density map 223 in a graphical user interface 215 on the display device 158. Each dose line or distribution may indicate the amount of radiation doses 225 that may be used in a specific area of the bulk electron density map. The bulk electron density map may comprise the reconstructed MR image where the defined segments are delimited and distinguished from each other e.g. by the electron density value assigned to each tissue or segment.

In step 209, a modification signal for modifying at least a first segment of the segments may be received. For example, the modification signal may be received in response to prompting a user of the therapy system 100 via the display device 158 in order to request the modification. In another example, the modification may automatically be received from algorithm 199 that, for example, detects parts or voxels being labelled for a given tissue, e.g., as cortical bone but exceeding a certain predefined diameter and thus are likely to be artefacts. These detected voxels may be indicated in the modification signal for modifying them, e.g., in order to assign them to water tissue. In the case of an automatic received modification, the display steps may be optional.

The modification may comprise a shape modification of the first segment and/or density modification of the first segment e.g. as shown by modification line 227 performed using modification tool 217. For example, if a bone tissue exceeds the predefined diameter, the shape of the bone tissue or segment may be modified by for example removing some voxels of the bone tissue.

For example, the first segment may comprise a first set of voxels having respective first values indicative of a first tissue e.g. a bone of the imaging volume. The first values may comprise electron density values. The reception of the modification signal may comprise the reception of a selection of one or more voxels of the first set of voxels. Those selected one or more voxels may be removed, in one example, from the first segment and added to an adjacent segment of the first segment (e.g. water). In another example, the selection may indicate a second value (i.e. another electron density value) for each of the selected voxels. For example, the second value may be input or entered into an input field of the graphical user interface 215. In another example, the second value may be automatically read from storage device 160 upon receiving a selection of one of the user interface elements 227. Each of the user interface elements 227 is associated with a second value indicative of a respective tissue e.g. Air. The second value indicates a second tissue of the imaging volume and thus the first values may be replaced by the second values for the selected voxels such that the selected voxels become part of the second tissue.

The selection of the one or more voxels may for example be performed by a movement (a drag action 227) of a cursor e.g. 217 and 219 of the graphical user interface 215 onto the one or more voxels. For example, the cursor may be configured to perform change only on a given number of segments but not all of them. The cursor may for example be configured such that the water tissue or segment cannot be modified by that cursor.

In another example, the receiving of the modification may comprise detecting by a sensor e.g. of the display device a touch action on the (touch sensitive) display device 158 indicative of the modification (e.g. indicative of the selection of the one or more voxels). The touch action may comprise a drag action.

In another example, the touch action may be performed by orienting an entry pen of the display device 158 towards the one or more voxels without contacting the display device 158.

In another example, the selection of the one or more voxels may indicate a maximum and a minimum value. For each of the one or more selected voxels a value (e.g. electron density) of the voxel may be compared with the maximum (minimum) value and if the value of the voxel is higher (smaller) than the maximum (minimum) value the value of the voxel is replaced by the maximum (minimum) value.

In another example, the modification signal may alter the electron density value for a whole tissue, e.g. the cortical bone tissue, to reflect a higher or lower electron density. This may be useful to adjust bone density (i.e. the electron density of the bone) to the age of a patient.

In another example, the modification signal may alter the electron density value for part of a tissue, e.g. increasing or decreasing the value in a certain region of cancellous bone. An example application would be to increase the bone-density in the femur head, knowing, that trabecular structures leave it more dense than the average cancellous bone. Another example application would be to decrease the bone-density in the region of the sacrum, knowing, that the bone is less dense in that region than the average cancellous bone.

In step 211, the bulk electron density map may be recreated using the modification signal, and the radiation dose distributions may be recalculated using the recreated bulk electron density map. Those recreated bulk electron density map and recalculated radiation dose distributions may be redisplayed in step 213 on the graphical user interface.

The displayed recreated electron density map and the recalculated radiation dose distributions may be used for controlling the irradiation of at least part of the imaging volume in step 213.

For example, step 211 may further comprise prompting the user for requesting an acknowledgment of the displayed recreated electron density map and the recalculated radiation dose distributions and in response to receiving the acknowledgment performing step 213.

In one example, steps 207)-211) may be repeated until receiving a confirmation of the (recreated) bulk electron density map. For example, for each repetition the method may prompt the user for requesting confirmation. In another example, the confirmation may be received from the algorithm 199 e.g. as soon as no discrepancy is detected in the redisplayed electron density map. For each repetition, the modification may be performed on the same segment as in the previous iteration or on another different segment. Upon receiving the confirmation the irradiation of at least part of the imaging volume may be controlled using the confirmed electron density map and the radiation dose distributions.

Figure 3:
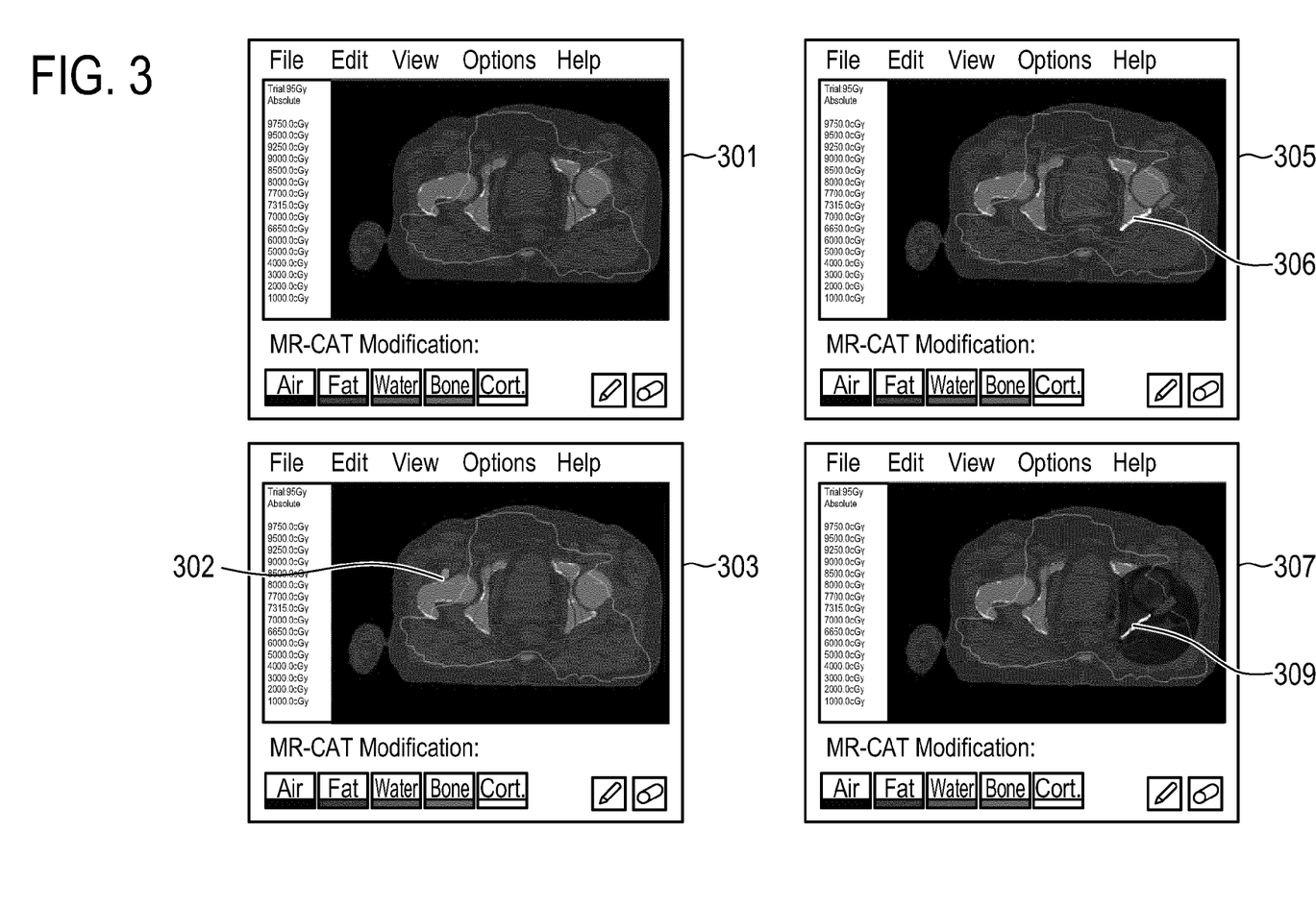
FIG. 3 shows an example of bulk electron density maps.

FIG. 3 shows an example of bulk electron density maps displayed together with radiation dose distributions.

The displayed graphical user interface 301 shows a first or initial radiation dose distribution on top of an electron density map. The radiation dose distribution in graphical user interface 301 is not yet modified.

The graphical user interface 303 illustrates a modification of the electron density map using an eraser tool 219 of the graphical user interface 303. The modification comprises deleting cortical bone voxels at position 302 of the electron density map. In this case the deleted voxels are assigned to cancellous bone tissue. This modification does not induce a change of the radiation dose distribution of graphical user interface 301, as can be seen by comparing iso-dose lines. The radiation dose distribution of graphical user interface 303 has been recalculated after the modification at position 302 has occurred. For example, the eraser tool 219 may not be available for certain tissues, e.g. water fat, since an underlying tissue must be defined by the system. Alternatively, an indication of the underlying tissue or a backup electron density value may be received from the user e.g. when using the eraser tool.

The graphical user interface 305 illustrates a modification of the electron density map that is performed using a user interface element 217 in the form of a tissue-specific pen. In this modification cortical bone voxels have been added at position 306. This modification, however, has induced a change in the radiation dose distribution compared to the radiation dose distribution of graphical user interface 301, as can be seen by comparing the isodose lines in the vicinity of the modification. The radiation dose distribution of graphical user interface 303 has been recalculated after the modification at position 306 has occurred. If the change is minor (smaller than a maximum shift value) using the initial MR image for the radiotherapy process, otherwise using the modified image for the radiotherapy process.

The graphical user interface 307 illustrates a modification of the electron density map that is performed, while viewing original MR image (in this case the inphase image) below the electron density map. The electron density map is then rendered transparent within the region of modification. This transparency may be steerable with keyboard or mouse interaction, such that the user can switch between viewing the electron density map and viewing the original MR image. The modification comprises adding cortical bone annotations with tissue pen at position 309. Thus, the image modification is based on true image content.

The modified radiation dose distributions may be displayed in graphical user interface 305 or 307 simultaneously or with a delay with the electron density map.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

LIST OF REFERENCE NUMERALS 100 therapy system
102 radiotherapy apparatus
104 mechanical actuator
106 magnetic resonance imaging module
108 ring mechanism
110 radio therapy source
112 multi-leaf beam collimator
114 radiation beam
116 rotational axis
117 rotational point
122 main magnet
124 cryostat
126 superconducting coil
128 compensation coil
130 low magnetic field zone
132 magnet axis
134 magnetic field gradient coil
136 magnetic field gradient coil power supply
138 imaging volume 140 radio frequency coil
142 radio frequency transceiver
144 subject
146 target volume
148 patient carrier
150 mechanical positioning system
152 computer system
154 hardware interface
156 processor
158 user interface
160 computer storage
162 computer memory
164 top distance
166 bottom distance
170 image magnet resonance data
172 diagnostic images
174 coordinates of target volume
178 radio therapy control signals
180 therapeutic apparatus control module
182 radio therapy apparatus control module
186 magnetic resonance imaging control module
188 image reconstruction module
194 radio therapy control signal generation module
199 program
215, 301, 303, 305, 307 graphical user interface.

The invention claimed is:

1. An apparatus, comprising:
a magnetic resonance imaging system;
a processor for controlling the apparatus; and
a memory containing machine executable instructions and a pulse sequence, wherein execution of the instructions causes the processor to control the apparatus to perform operations comprising:
(a) acquiring magnetic resonance data from an imaging volume using the magnetic resonance imaging system and the pulse sequence;
(b) segmenting the magnetic resonance data into a plurality of segments indicating respective tissues in the imaging volume;
(c) creating a bulk electron density map of the imaging volume from the plurality of segments;
(d) displaying, on a display device of a graphical user interface, the bulk electron density map and radiation dose distributions for the imaging volume, wherein the radiation dose distributions are determined using the bulk electron density map;
(e) after displaying on the display device the bulk electron density map and radiation dose distributions for the imaging volume, receiving a modification signal for modifying at least a first segment of the segments;
(f) recreating the bulk electron density map using the modification signal, and recalculating the radiation dose distributions using the recreated bulk electron density map; and
(g) displaying the recreated bulk electron density map and the recalculated radiation dose distributions on the display device of the graphical user interface.

2. The apparatus of claim 1, wherein execution of the instructions further causes the processor to repeat steps (e) through (g) until receiving from a user a confirmation of the recreated bulk electron density map.

3. The apparatus of claim 1, wherein the first segment comprises a first set of voxels having respective first values indicative of a first tissue of the imaging volume, and wherein:
receiving the modification signal comprises receiving a selection of one or more voxels of the first set of voxels, wherein the selection is indicative of a second value for each of the selected voxels, the second value indicating a second tissue of the imaging volume; and
recreating the bulk electron density map comprises replacing the first values by the second values for the selected voxels.

4. The apparatus of claim 1, wherein the first segment comprises a first set of voxels having respective first values indicative of a first tissue of the imaging volume, and wherein:
receiving the modification signal comprises receiving a selection of one or more voxels of the first set of voxels, wherein the selection is indicative of a maximum value; and
in case a first value of a voxel of the selected voxels is higher than the maximum value, recreating the bulk electron density map comprises replacing that first value by the maximum value, wherein the maximum value is indicative of a second tissue of the imaging volume.

5. The apparatus of claim 1, wherein the first segment comprises a first set of voxels having respective first values indicative of a first tissue of the imaging volume, and wherein;
receiving the modification signal comprises receiving a selection of one or more voxels of the first set of voxels, wherein the selection is indicative of a minimum value; and
in case a first value of a voxel of the selected voxels is smaller than the maximum value, recreating the bulk electron density map comprises replacing that first value by the minimum value, wherein the minimum value is indicative of a third tissue of the imaging volume.

6. The apparatus of claim 1, wherein the first segment comprises a first set of voxels all having respective first values indicative of a first tissue of the imaging volume, and wherein:
receiving the modification signal comprises receiving a selection of one or more voxels of the first set of voxels; and
recreating the bulk electron density map comprises removing the selected one or more voxels of the first segment and assigning the selected one or more voxels third values which are different from the first values.

7. The apparatus of claim 1, wherein the modification signal for modifying the first segment is received in response to a movement by a user of a cursor of the graphical user interface onto at least part of the first segment for selection of the at least part of the first segment.

8. The apparatus of claim 1, wherein the display device comprises a touch sensitive display device, the apparatus further comprising a sensor, and wherein the reception of the modification signal comprises: detecting by the sensor a touch action by a user on the display device indicative of the modification.

9. The apparatus of claim 8, further comprising an entry pen wherein the modification signal is generated by orienting the entry pen towards at least part of the first segment without contacting the display device for selection of the at least part of the first segment.

10. The apparatus of claim 8, further comprising an entry pen, wherein the touch action comprises interaction of the entry pen with the display device, or a user finger touch of the display device.

11. The apparatus of claim 8, wherein the touch action comprises a drag action having a starting point and an ending point in the first segment, wherein the modification is performed along a line between the starting and ending points.

12. The apparatus of claim 2, wherein execution of the instructions further causes the processor to: display an MR image of the imaging volume before receiving the confirmation.

13. The apparatus of claim 2, wherein the repeating of steps (e) through (g) is performed for a second segment different from the first segment.

14. The apparatus of claim 1, wherein execution of the instructions further causes the processor to control the apparatus to use the displayed electron density map and the radiation dose distributions for controlling irradiation of at least part of the imaging volume.

15. A method, comprising:
(a) receiving magnetic resonance data from an imaging volume;
(b) segmenting the magnetic resonance data into a plurality of segments indicating respective tissues in the imaging volume;
(c) creating a bulk electron density map of the imaging volume from the plurality of segments;
(d) displaying on a display device of a graphical user interface the bulk electron density map and radiation dose distributions for the imaging volume, wherein the radiation dose distributions are determined using the bulk electron density map;
(e) after displaying on the display device the bulk electron density map and radiation dose distributions for the imaging volume, receiving a modification signal for modifying at least a first segment of the segments;
(f) recreating the bulk electron density map using the modification signal, and recalculating the radiation dose distributions using the recreated bulk electron density map; and
(g) displaying the recreated bulk electron density map and the recalculated radiation dose distributions on the display device of the graphical user interface.

16. A tangible computer program product comprising a tangible media having stored thereon computer executable instructions to cause a processor to perform the method of claim 15.

17. The method of claim 15, further comprising repeating steps (e) through (g) until receiving from a user a confirmation of the recreated bulk electron density map.

18. The method of claim 15, further comprising:
a user moving a cursor of the graphical user interface onto at least part of the first segment for selection of the at least part of the first segment; and
generating the modification signal for modifying the first segment in response to the movement of the cursor by the user.

19. The method of claim 15, further comprising:
detecting by a sensor a touch action on the display device indicative of the modification; and
generating the modification signal for modifying the first segment in response to the touch action.

20. The method of claim 15, further comprising using the displayed electron density map and the radiation dose distributions for controlling irradiation of at least part of the imaging volume.

* * * * *